(12) United States Patent
Thundat et al.

(10) Patent No.: US 6,311,549 B1
(45) Date of Patent: Nov. 6, 2001

(54) MICROMECHANICAL TRANSIENT SENSOR FOR MEASURING VISCOSITY AND DENSITY OF A FLUID

(75) Inventors: Thomas G. Thundat, Knoxville, TN (US); Patrick I. Oden, Plano, TX (US); Robert J. Warmack, Knoxville, TN (US); Eric Laurent Finot, Torcy (FR)

(73) Assignee: U T Battelle LLC, Oak Ridge, TN (US)

( * ) Notice: Subject to any disclaimer, the term of this patent is extended or adjusted under 35 U.S.C. 154(b) by 0 days.

(21) Appl. No.: 09/401,865

(22) Filed: Sep. 23, 1999

(51) Int. Cl.[7] .......................... G01N 11/10; G01N 13/02; G01N 27/00
(52) U.S. Cl. ................. 73/54.24; 73/54.25; 73/54.41; 73/24.05; 73/32 A
(58) Field of Search ................. 73/54.24, 54.25, 73/54.26, 54.41, 54.01, 24.05, 32 A

(56) References Cited

U.S. PATENT DOCUMENTS

| | | | |
|---|---|---|---|
| 3,393,553 | * 7/1968 | Kleinschmidt | 73/54 |
| 3,777,550 | * 12/1973 | Kleinschmidt | 73/59 |
| 3,930,399 | 1/1976 | Munk | 73/55 |
| 4,141,253 | 2/1979 | Whitehead, Jr. | 73/727 |
| 4,277,971 | 7/1981 | Drzewiecki et al. | 73/55 |
| 4,302,965 | 12/1981 | Johnson et al. | 73/55 |
| 4,426,878 | 1/1984 | Price et al. | 73/55 |
| 4,437,337 | * 3/1984 | Fenrick | 73/54 |
| 4,729,237 | 3/1988 | Suzuki et al. | 73/54 |
| 4,741,200 | 5/1988 | Hammerle | 73/54 |
| 4,799,378 | * 1/1989 | Portman, Jr. et al. | 73/54 |
| 4,864,849 | 9/1989 | Wright | 73/57 |
| 4,890,480 | * 1/1990 | Young | 73/32 A |
| 4,905,499 | 3/1990 | Miura et al. | 73/32 A |
| 4,905,503 | 3/1990 | Langrick | 73/55 |
| 4,920,787 | 5/1990 | Dual et al. | 73/54 |
| 4,926,682 | 5/1990 | Holm-Kennedy et al. | 73/54 |
| 5,157,962 | 10/1992 | Fitzgerald et al. | 73/54.24 |
| 5,224,375 | 7/1993 | You et al. | 73/54.08 |
| 5,317,908 | 6/1994 | Fitzgerald et al. | 73/54.26 |
| 5,339,258 | * 8/1994 | Stabinger et al. | 364/558 |
| 5,445,008 | 8/1995 | Wachter et al. | 73/24.06 |
| 5,494,639 | 2/1996 | Grzegorzewski | 422/82.01 |
| 5,565,620 | * 10/1996 | Bohlin | 73/54.25 |
| 5,670,709 | 9/1997 | Gallagher | 73/54.24 |
| 5,698,773 | 12/1997 | Blom et al. | 73/54.18 |
| 5,719,324 | 2/1998 | Thundat et al. | 73/24.01 |
| 6,044,694 | * 4/2000 | Anderson et al. | 73/54.41 |
| 6,182,499 | * 2/2001 | McFarland et al. | 73/24.06 |

OTHER PUBLICATIONS

Albrecht et al., Microfabrication of Cantilever Styli for the Atomic Force Microscope, J of Vacuum Science & Technology A, 8, 3386– (1990).

Thundat, et al., Microcantilever Sensors, Microscale Thermophysical Engineering, 1:185–199, 1997.

Oden, et al., Viscous drag measurements Utilizing Microfabricated Cantilevers, Appl. Phys. Lett. 68 (26), 38141, (1996).

* cited by examiner

Primary Examiner—Helen Kwok
Assistant Examiner—David J. Wiggins
(74) Attorney, Agent, or Firm—J. Herbert O'Toole; Hardaway/Mann IP Group; Nexsen Pruet Jacobs & Pollard, LLC

(57) ABSTRACT

A method and apparatus for measuring the viscosity and/or specific density of a fluid utilizes a microcantilever vibrated in the analyte fluid. The source of vibration is switched on and off and the transient behavior or decay in amplitude of the vibration is monitored. The method is particularly useful for the measurement of process conditions in remote locations in real time.

18 Claims, 3 Drawing Sheets

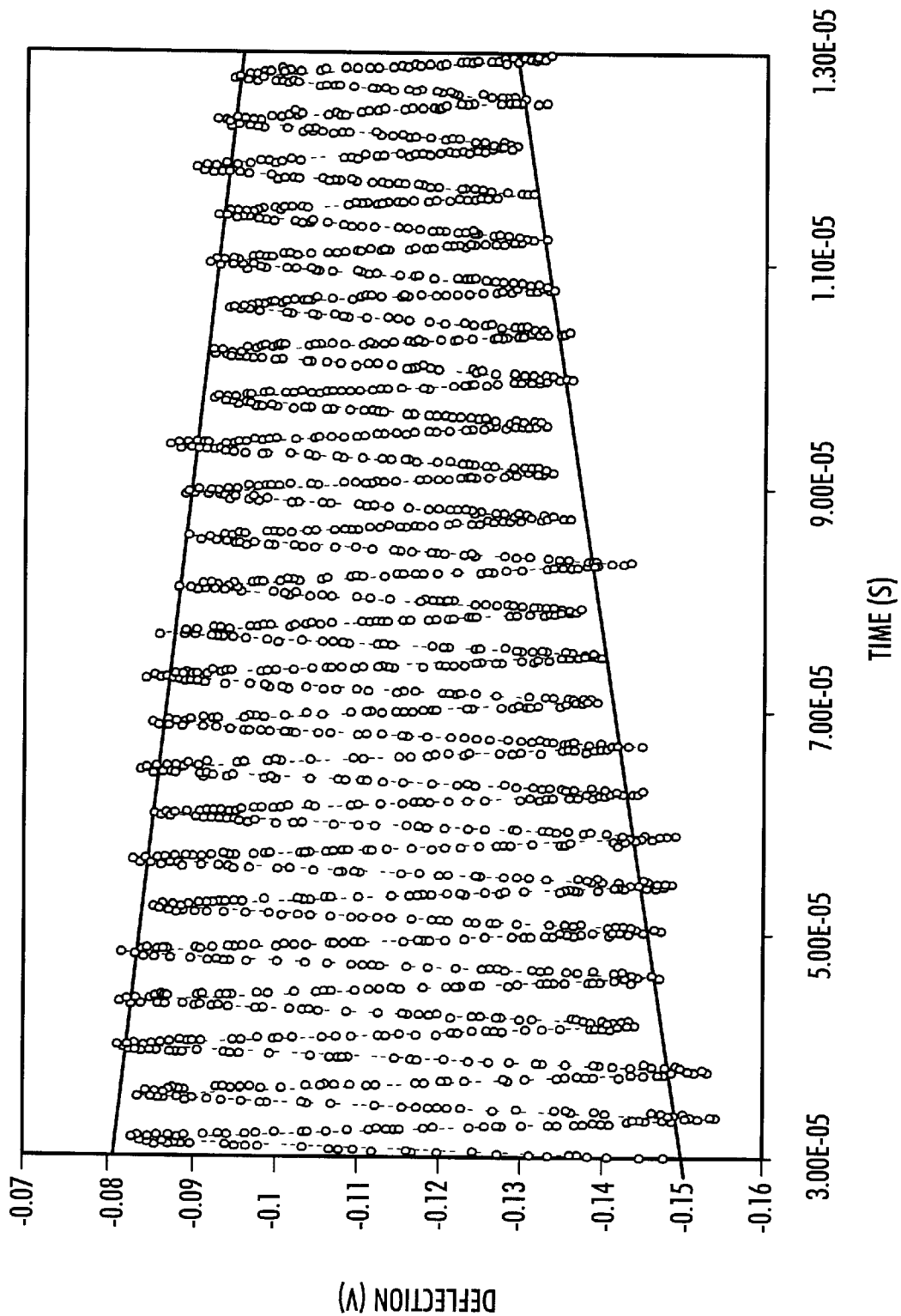

US 6,311,549 B1

MICROMECHANICAL TRANSIENT SENSOR FOR MEASURING VISCOSITY AND DENSITY OF A FLUID

RELATED APPLICATIONS

This application is related to pending U.S. patent application Ser. No. 09/042,601 filed Mar. 16, 1998; and, Ser. No. 09/281,032 filed Mar. 30, 1998; and, Ser. No. 09/281,256 filed Mar. 30, 1998.

This invention was made with Government support under Contract No. DE-AC05-96OR22464 awarded by the U.S. Department of Energy to Lockheed Martin Energy Research Corporation, and the Government has certain rights in this invention.

BACKGROUND OF THE INVENTION

1. Field of the Invention

This invention relates to apparatus and methods for the accurate determination of viscosity, density or both of very small volumes of fluids.

2. Prior Art

The atomic force microscope (AFM) was first demonstrated by Binnig and co-workers at IBM in Switzerland. In the AFM, the tip of a flexible cantilever stylus is rastered over the surface of a sample and the movement of the tip of the cantilever is monitored as a measure of minute forces characteristic of surfaces at the atomic level. Demonstration of this principle led to rapid development of microcantilevers [(Albrecht et al., *J. Vac. Sci. Technol*, 8, 3386 (1990)]. The concept of micromechanical and microelectromechanical detection devices has been developed for a number of analytical uses. Wachter et al., U.S. Pat. No. 5,445,008 describes the use of vibrated microcantilevers having a chemical coating as a detector for the presence of specific chemical entities. Thundat, et al. in *Appliance Manufacturer*, April 1997, 57 (1997) and *Microscale Thermophysical Engineering* 1, 185 (1997) describe developments of the microelectromechanical sensors (MEMS) for the measurement of chemicals and physical phenomena including the use of sensors to determine concentrations of glycerol in water based on viscosity.

U.S. Pat. No. 5,719,342 to Thundat et al., addresses additional methods for analysis using MEMS devices particularly directed to induced stress in the microcantilever.

U.S. Pat. No. 5,130,257 to Bear et al., discloses a viscosity sensor fabricated using a surface transverse wave device for use in the measurement of viscosity.

Oden et al., *Appl. Phys. Lett.,* 68, 3814 (1996) discloses method for the measurement of viscosity using microfabricated cantilevers in a confined medium. The frequency of vibration of an isolated vibrating cantilever is measured in different solutions.

U.S. Pat. No. 5,494,639 to Grzegorzewski discloses a disposable biosensor which uses a vibrating member beneath a cell to accurately measure blood coagulation time as a function of viscosity.

The foregoing methods are attempts to find an alternative to the instruments most currently used to measure viscosity of both liquids and gases. These are instruments which perform the analysis by a comparison with a "control fluid." For this reason, measurements are still routinely done using instruments such as the Redwood viscometer, the Couette or rotational concentric-cylinder viscometer (MacMichael or Stormer viscometer), the Rotating Sphere viscometer, the Sayboult Falling Body viscometer, the Vibrating String viscosity meter and the thickness-shear mode resonators. All of these methods require comparatively large volumes and bulky equipment. The need remains for a small reliable and inexpensive instrument which can measure the viscosity or specific density of small amounts of a liquid or gas and which can be used in difficult-to-access locations.

BRIEF SUMMARY OF THE INVENTION

It is an object of this invention to provide a microminiaturized instrument for the measurement of viscosity and density in liquids and gases. It is a further object of this invention to provide such an instrument which is reliable and inexpensive in comparison with other instrumentation available.

It is a further object to provide a means for profiling the viscosity in a non-inhomogeneous fluid.

It is a further object of this invention to provide means for detecting viscosity and density of very small sample volumes of fluids; to determine viscosity and density of fluids in small confined spaces; to determine kinetics of chemical, biological, and physical reactions by measuring viscosity and density; and, to determine the completeness of chemical, biological, and physical reactions by measuring the viscosity and density.

These and other objects are met by using microcantilevers having typical dimensions of 50–200 $\mu$m in length, 10–40 $\mu$m in width, and 0.3–3 $\mu$m in thickness. When such a microcantilever is driven into resonance, the resonance frequency, amplitude and Q-value varies with the viscosity and the density of the medium surrounding the cantilever. More particularly, according to this invention, the cantilever is excited into resonance by an external means for a finite amount of time until a stable resonance amplitude is established. After that period, the external excitation is switched off and the transient behavior (decay) of the vibration is recorded. The resonance frequency, amplitude and Q factor are determined from the transient spectrum. The decay in amplitude of vibration can be used to determine the density of the material. Numerous methods for measuring the vibration of the cantilever are available and a multiplicity of cantilevers can be used for the determination of a wide range of densities.

BRIEF DESCRIPTION OF THE DRAWINGS

FIG. 3(*b*) shows the corresponding transient response of a cantilever.

FIG. 4 is a trace of the transient response of a cantilever.

DETAILED DESCRIPTION OF THE INVENTION

Figure 1:
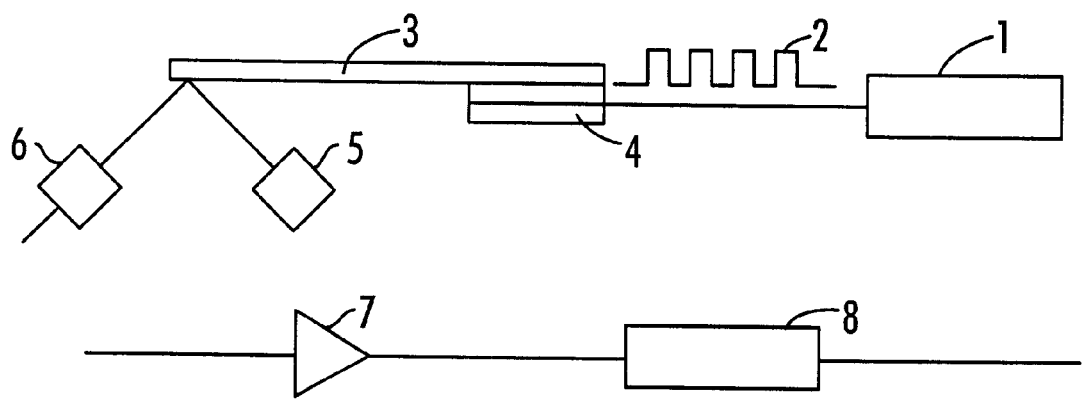
FIG. 1 is a schematic diagram illustrating the components of this invention.

A MEMS device can be constructed using available or easily fabricated components. The microcantilevers used are commercially available from several sources, and may include those conventionally used in scanning force microscopy. Alternatively, the microcantilever may be prepared from various ceramics metals and semiconductor materials by methods well known to those familiar with the fabrication of microelectronic devices and according to the method of the aforementioned Albrecht et al. reference. Likewise, a mounting block with an inventive piezoelectric exciting device is commercially available, as is a mounting stage for the cantilever and laboratory base. Detection methods may be optical beam deflection, optical interference, capacitance, piezoresistance, or electron tunneling. On the basis of familiarity, we prefer optical methods such as those described in the Wachter et al. patent, although one or more of the other methods described above may be suitable for liquids with a high degree of opacity or density.

The technique involve exciting the cantilever into resonance frequency by an external means such as a piezoelectric crystal or by electrostatic means, or electromagnetic, or photoinduced, or the like as are known in the art. The microcantilevers can also be excited using a photothermal technique where the light source is used in a pulse mode to impart energy to the cantilever. Microcantilevers can also be excited using acoustic waves. It may take many pulses to excite the microcantilevers into resonance. Because the square pulses contain all the Fourier components, a cantilever of any natural resonance frequency can be excited using square pulse excitation. The form of the excitation amplitude can be periodic at or near the resonant frequency of the cantilever and can be pure harmonic, square, or other arbitrary waveform. A pure harmonic waveform to induce the maximum amplitude resonance of the cantilever may be used. An impulse or rectangular pulse can also be used. Once the cantilever is excited into resonance, the excitation source is switched off and the transient behavior of the microcantilever deflection is recorded. In the case of rectangular pulses, the transient response occurs at the beginning and at the end of the pulse. The cantilever resonance amplitude drops off exponentially with time. From the zero crossing of the deflection, the resonance frequency (crossing per unit time) can easily be found. The Q-factor can be determined from decay curve of the amplitude (from the logarithmic decrement).

The mathematical expression for viscosity and density of the fluid can be derived as follows. Let L, W, and T be the length, width, and thickness of the cantilever. The density of the cantilever is taken as $\rho_c$. The cantilever resonates in vacuum with a resonance frequency, $\omega_o$ ($2\pi f^o$) and a quality factor $Q_o$. The finite Q-factor in vacuum is mainly due to internal energy loss. However, when operated in a fluid, the resonance frequency and Q-factor change due to energy loss due to viscosity. The equation of motion of the cantilever in a medium can be written as:

$$EI\frac{\partial^2 u}{\partial x^2} + (b_0 + b)\frac{\partial u}{\partial t} + (M_c + M_f)\frac{\partial^2 u}{\partial t^2} = 0 \tag{1}$$

where E is the Young's modulus, I is the moment of inertia, $b_o$ is the intrinsic damping of the cantilever, $M_c$ is the mass per unit length of the cantilever, $M_f$ us the induced mass (mass of fluid moving along with the cantilever per unit length), and u is the cantilever displacement at distance x from the fixed end of the cantilever.

The moment of inertia of a rectangular cantilever is given by:

$$I = \frac{WT^3}{12} \tag{2}$$

where W is the width and T is the thickness of the cantilever. The intrinsic damping $b_o$ can be determined from the resonance characteristics of the cantilever in vacuum ($w_o$ and $Q_o$. The intrinsic damping, $b_o$, can be written as:

$$b_c = \frac{\omega_o \rho_c WT}{Q_o} \tag{3}$$

where $w_o$ and $Q_o$ are the resonance frequency and the quality factor, respectively of the cantilever in vacuum. The damping due to viscosity of the fluid is given by:

$$b_f = \frac{W}{T}M_f\left(\frac{\omega}{\sqrt{2R_K}}\right) \tag{4}$$

Where w is the angular frequency, $\eta$ is the viscosity of the fluid and $R_k$ is the Reynold's number of the fluid defined as:

$$R_K = W^2\left(\frac{\rho}{\eta}\right)\omega \tag{5}$$

The mass per unit length, $M_c = p_c WT$:

$$M_c = \rho_c WT \tag{6}$$

The induced $M_f$ equals:

$$\left(\frac{W}{T}\right)\rho_c \omega u\left(1 + \frac{4}{\sqrt{2R_K}}\right) \tag{7}$$

Solution for the equation of motion is complex quantity. The angular resonance frequency is given by:

$$\omega = \left(\sqrt{\frac{3.52^2 EI}{(M_o + M)L^4}}\right) + i\left(\frac{b_o + b}{2(M_o + M)}\right) \tag{8}$$

Equation 8 is a complex number of form, X+iY.

The measured angular frequency is:

$$\omega_{real} = \sqrt{X^2 + Y^2} \tag{9}$$

And the full width at $2_{-0.5}$ of the maximum angular frequency is:

$$\Delta\omega = Y \tag{10}$$

The Q-factor can be expressed as, $$Q = \omega/\Delta\omega$$

defining $M^* = 2(M_c + M_f)$ and $b^* = (b_v + b_f)$ in Eq.1, $$M^* = \frac{C}{\omega^2}\left(\frac{Q^2}{Q^2 - 1}\right) \text{ and } b^* = \frac{C}{\omega}\left(\frac{Q^2}{Q^2 - 1}\right) \text{ with } C = 3.52^2 EI/L^4$$

Therefore, $M_f$ and $b_f$ can now be written as:

$$M = M^*/2 - M_c \tag{11}$$

$$b_f = b^* - b_c \tag{12}$$

Using Eq. 4, Reynold's number can now be expressed as:

$$R_K = \frac{1}{2}\left[\left(\frac{M_f}{b_f}\right)\frac{W\omega}{T}\right]^2 \quad (13)$$

Now $R_x$ can be calculated using the resonance frequency, Q-factor, and the amplitude of vibration in vacuum and in the medium. the length, width, and the thickness of the cantilever as well as the density of the cantilever material is known apriori. Once the Reynold's number and $M_f$ are known, the density and the viscosity of the medium can be calculated as follows:

$$\rho = \frac{M_f T}{W\omega u\left(1 + \frac{4}{\sqrt{2R_K}}\right)} \quad (14)$$

The viscosity of the medium is given by:

$$\eta = \frac{W^2 \rho_f \omega}{R_K} \quad (15)$$

Initially the cantilever is calibrated in vacuum or in a fluid with known properties for determining its intrinsic resonance properties. Later the cantilever can be resonated in unknown fluids. Or the cantilever can be calibrated in vacuum and a fluid of known viscosity and density to determine the relative changes in viscosity and density observed with respect to a fluid of known viscosity and density.

Another advantage is that this technique is the speed by which measurements can be carried out. The typical time involved is in the range of sub milliseconds to sub microseconds.

As can be seen from the derivation of equation (15) the method has two inherent advantages. The cantilever can be recalibrated as needed by testing in a vacuum or a fluid of known properties. Any drift in the instrument can be immediately identified. In addition, different cantilevers can be compared to each other so that there is no instrumental error resulting from the fabrication of the devices. A second advantage is that, for a given device, comparisons between fluids can be readily made. As noted earlier, for most industrial uses, it is not the absolute viscosity but the viscosity relative to another fluid which is important. A third advantage is magnetic excitation. Magnetic excitation can be achieved by attaching a magnetic particle or evaporating a magnetic film such as Cr or Co or their alloys to the apex of the cantilever. For process control, this device quickly senses the direction and the magnitude of any change in viscosity. Since viscosity is affected by temperature, the device may be used to identify a process or operational change before a bulk viscosity or density change could be quickly measured.

Because cantilevers can be readily fabricated in one- or two-dimensional arrays, inhomogeneities of viscosity or density in the monitored fluid can be sensed. Individual cantilevers in the arrays sense physical properties in their immediate vicinity. For example, a one-dimensional array could be placed in a fluid stream, such as a pipe, to measure any inhomogeneities or gradients in viscosity or density of the fluid flow.

Microcantilevers can be excited and their movement measured in a variety of manners. Excitation may be by piezoelectric, piezoresistive methods, by capacitive, photothermal, electrostatic, or acoustic techniques. Movement of the cantilever is preferably measured by reflection of light from the tip of the microcantilever but may also be measured piezoelectricly, piezoresistively, and by the methods disclosed in U.S. Pat. Nos. 5,440,008 and 5,719,324.

Figure 2:
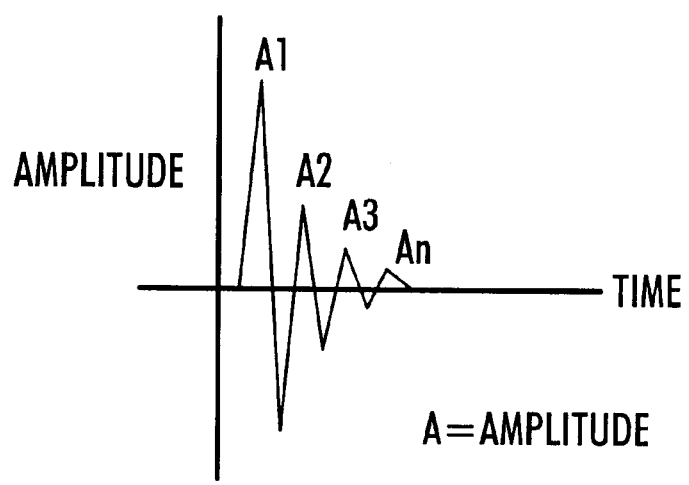
FIG. 2 is an illustration of the signal which is used to discern the viscosity and density of a fluid medium.
Figure 3:
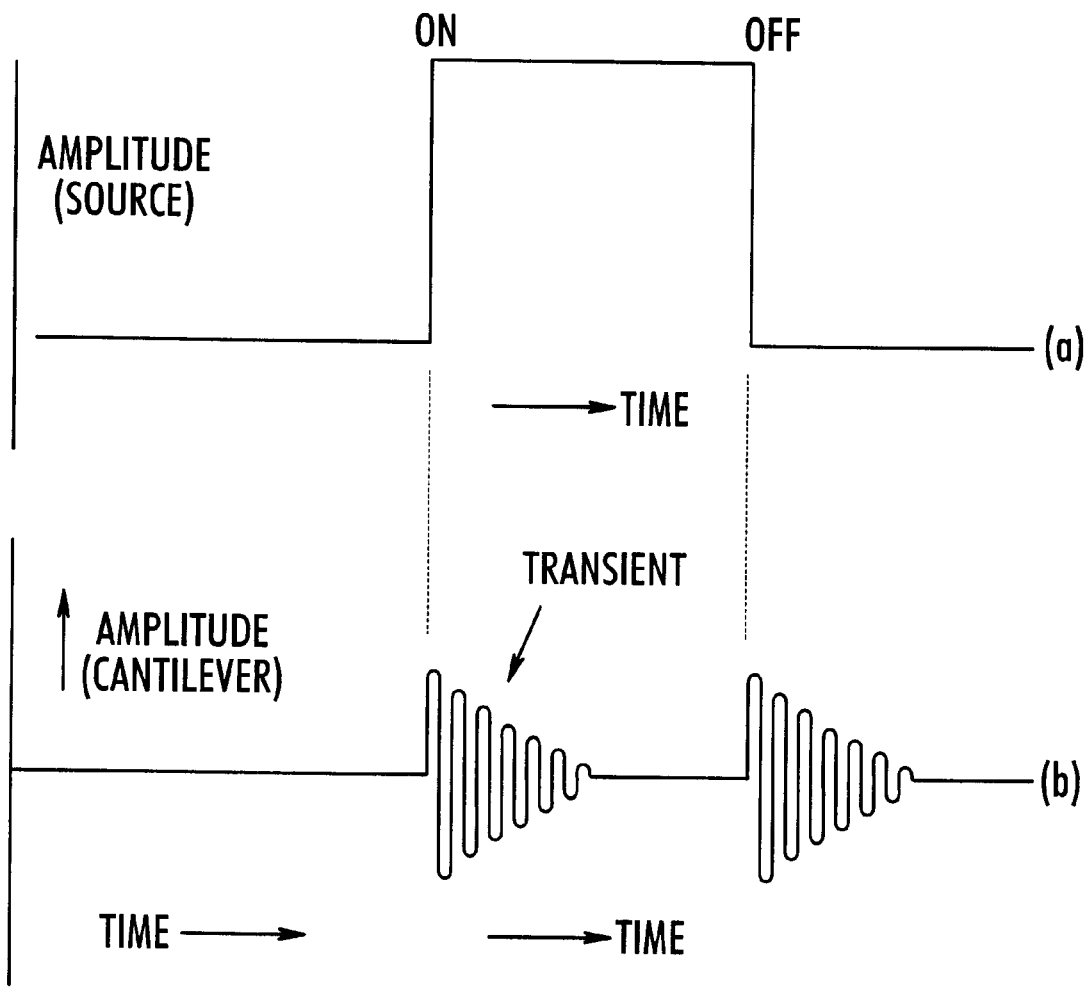
FIG. 3(*a*) shows a square wave signal used to excite a cantilever.

An exemplary device for measuring viscosity and density is shown in FIG. 1. An oscillator circuit 1 generates a square wave signal 2 which energizes a device 4 such as a piezoelectric transducer to cause a cantilever 3 to resonate. The resonance is detected, in the example, by shinning a light from laser diode 5 onto the tip of cantilever 3. The reflected light impinges upon position sensitive diode 6. The signal from PSD 6 is amplified (7) and analyzed at amplitude measuring circuit 8. The display of the result form the measurement is shown in FIG. 2 as a plot of amplitude versus time for the decay of resonance when the stimulation is interrupted. FIG. 3 illustrates the relationship between the square wave signal and cantilever response.

The method of this invention may be used to determine many physical parameters and for process and quality control. The sensors are very small and may be located in remote and even hazardous locations. Viscosity/specific density provides a good indication of the completeness of a chemical reaction and provides a nearly instantaneous indication of when a process stream condition changes. Leaks, especially gas leaks, are quickly identified at the source.

The devices are also useful in kinetic studies, especially using shock tubes to study reaction process.

Because this method is based on relative changes in the successive amplitudes rather than absolute amplitudes, this method can be used for measuring viscosity and density in noisy environments. However, when used in severely interfering noise environments, a reference cantilever can be used to avoid transients caused by noises. For example, acoustic noises in the environments can produce transient motion of a cantilever. Using a reference cantilever the noise contribution from the transient can be filtered using wavelet or Fourier transform analysis. The same approach can be used for other interference such as noise introduced by temperature variation.

The invention will be described in terms of an example which illustrates the operation of the invention. The example is not limitative of the invention and modifications obvious to those with skill in this art are included within the scope of applicants' invention.

EXAMPLE 1

A microcantilever may be fabricated to specify length, width and thickness. The microcantilever is attached, at its base, to a piezoelectric device which is energized by a square wave generator. The microcantilever may be first characterized in a vacuum to determine the resonance frequency and Q-factor by observing the transient response of the cantilever. This is the calibration of the cantilever.

The chamber is then opened to admit a gas, pure nitrogen, and allowed to equilibrate at a pressure of 760 mm of Hg. The decay curve of the microcantilever is determined as before and plotted as illustrated in FIG. 4. It is noted that the absolute magnitude of the amplitude is not critical, only the decrement. The experiment was repeated using Argon and He. The longarithimic decrement of the amplitude σ is given by equation (16):

The value of Q can be determined from the decay curve of the amplitude. The value of the resonance frequency can be determined from the center crossing of the decay curve. The logarithmic decrement of the amplitude δ is given by $$\delta = \left[\frac{A_{n+1}}{A_n}\right] \qquad (16)$$

Where $A(n+1)$ and $An$ are successive amplitudes The Q factor is given as $Q=\pi/\delta$.

Density and viscosity of some gases:

| Gas | $\rho$ (kg/m3) | $\eta$ ($\mu$Pa-s) |
|---|---|---|
| Air | 1.29 | 18.6 |
| N2 | 1.25 | 17.9 |
| O2 | 1.43 | 20.8 |
| Ar | 1.78 | 22.9 |
| CO | 1.25 | 17.8 |
| CH4 | 0.71 | 11.2 |
| H2 | 0.0899 | 9.0 |

Experimental results obtained from transient techniques for density and viscosity closely follows published values. This technique was also extended to liquids.

What is claimed is:

1. A method for the determination of viscosity and density of a fluid comprising:
    a) providing at least one microcantilever, a means to vibrate said at least one microcantilever, and a means to detect motion of said at least one microcantilever;
    b) calibrating said at least one microcantilever by observing decay in the amplitude of vibration of said microcantilever when said vibratory means is terminated using a vacuum or a known fluid as a standard;
    c) measuring the decay in amplitude of vibration of the at least one cantilever in an unknown fluid; and
    d) calculating the viscosity and density of the unknown fluid by reference to the standard.

2. A method according to claim 1 wherein the fluid is a gas.

3. A method according to claim 2 wherein the gas is a pure, ideal gas.

4. A method according to claim 2 wherein the gas is a mixture of gasses.

5. A method according to claim 1 wherein the fluid is a liquid.

6. A method according to claim 5 wherein the liquid is a neat liquid.

7. A method according to claim 5 wherein the liquid is a mixture.

8. A method according to claim 1 wherein the means to vibrate said at least one microcantilever is selected from the group consisting of piezoelectric crystals, electromechanical devices, acoustic waves, magnetic, electrical, photothermal sources and photoinduction devices.

9. A method according to claim 8 wherein the means to vibrate is operated in a selected from the group consisting of pure harmonic, impulse or rectangular pulse mode.

10. A method according to claim 9 wherein the means to vibrate is operated in a rectangular excitation mode.

11. A method according to claim 1 wherein the means to detect motion of said at least one microcantilever is selected from the group consisting of photo-optic detectors, piezoresistive detectors, piezoelectric detectors, capacitive detectors and electron tunneling.

12. A method for the determination of the completeness of a chemical reaction or process comprising observing the change in the viscosity of solution or mixture using the method according to claim 1.

13. A method for determining the presence of inhomogentetics and gradients in a flowing fluid comprising observing the viscosity or density using a method according to claim 1.

14. A method according to claim 1 wherein the at least one microcantilever is an array of microcantilevers arranged in a pattern.

15. A method according to claim 14 wherein said pattern is selected from the group consisting of one-dimensional and two-dimensional patterns.

16. A method according to claim 14 wherein said array of cantilevers is used to map variations in viscosity and density of a fluid.

17. A method according to claim 16 wherein the fluid is a flowing fluid.

18. A method according to claim 1 further comprising at least one reference cantilever.

\* \* \* \* \*